United States Patent [19]

Ensanian

[11] 4,133,722
[45] Jan. 9, 1979

[54] PROCESS FOR DETERMINING PROPERTIES OF MATERIALS

[76] Inventor: Minas Ensanian, P.O. Box 98, Eldred, Pa. 16731

[21] Appl. No.: 765,648

[22] Filed: Feb. 4, 1977

Related U.S. Application Data

[60] Continuation-in-part of Ser. No. 754,571, Dec. 27, 1976, abandoned, which is a division of Ser. No. 574,360, May 5, 1975, Pat. No. 4,006,063, which is a continuation of Ser. No. 79,033, Oct. 8, 1970, abandoned.

[51] Int. Cl.$^2$ .................... G01N 27/46; G01B 7/16
[52] U.S. Cl. .................... 204/1 T; 73/763; 324/29; 324/71 R
[58] Field of Search .................... 324/71 R, 72, 72.5, 324/29; 73/88 R; 204/1 T, 195 R

[56] References Cited

U.S. PATENT DOCUMENTS

| | | | |
|---|---|---|---|
| 3,134,077 | 5/1964 | Hutchins et al. | 324/72.5 |
| 3,808,105 | 4/1974 | Rozeanu | 204/1 T |
| 4,006,063 | 2/1977 | Ensanian | 204/1 T |

FOREIGN PATENT DOCUMENTS

1044532 10/1966 United Kingdom ............... 204/195

*Primary Examiner*—G. L. Kaplan
*Attorney, Agent, or Firm*—Ashlan F. Harlan, Jr.

[57] ABSTRACT

A process and apparatus applicable to products which are or can be made electrically conductive for the purpose of measuring information encoded in them as a result of the manufacturing steps employed. Elemental mechanogalvanic potentials reflect a measure of the total information content of a product and are generated when the product serves as an electrode and where a second electrode with a rollable solid electrolyte in contact with the product rolls over it generating data related to the elemental constituents of the product. Mappings or numerical matrices whose elements are the mechanogalvanic potentials can be the basis of extensive important analysis by conventional mathematical procedures.

27 Claims, 19 Drawing Figures

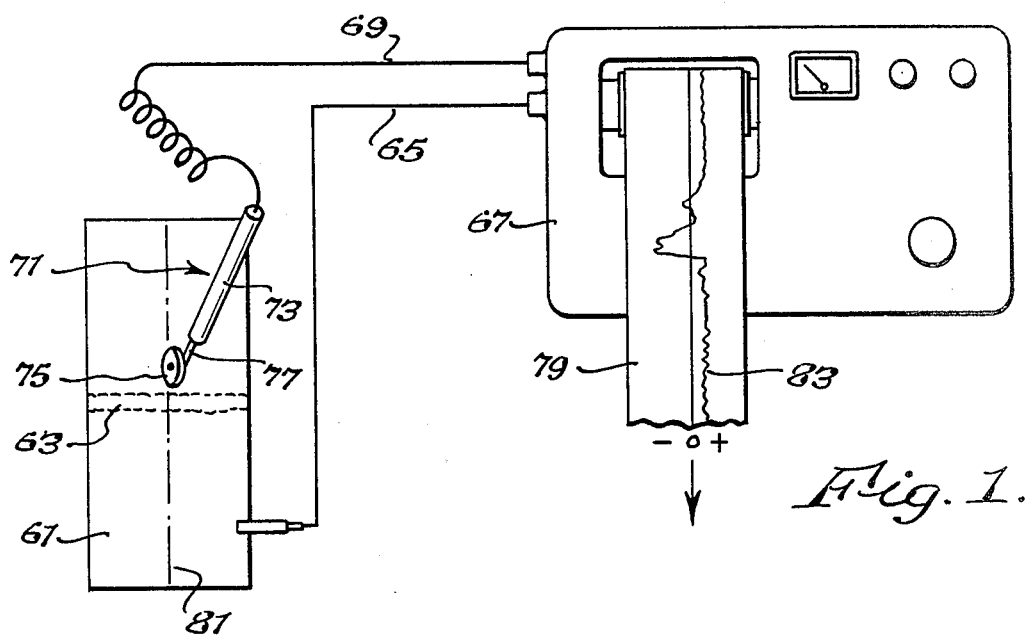
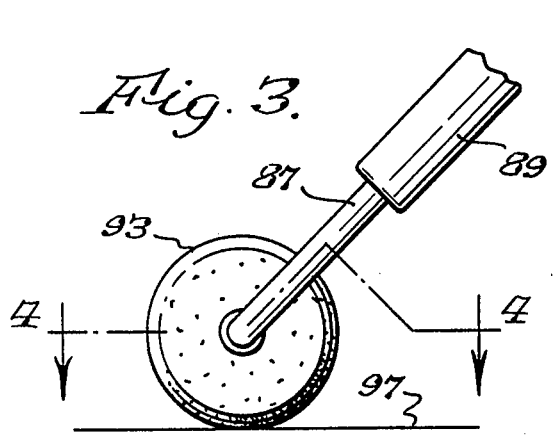
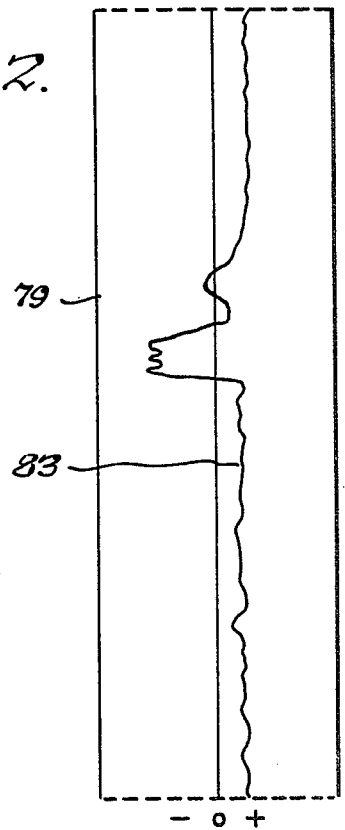
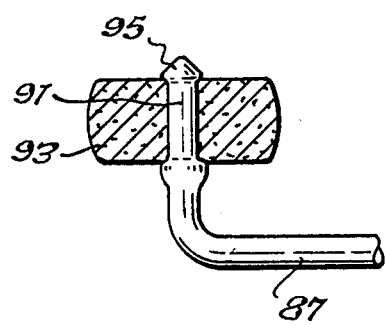
Fig. 1.
Fig. 2.
Fig. 3.
Fig. 4.

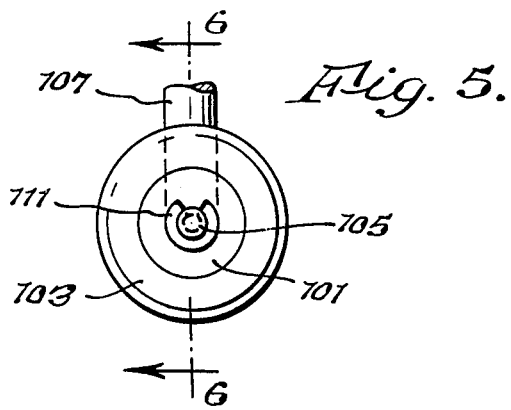
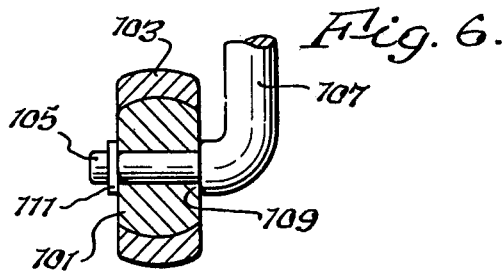
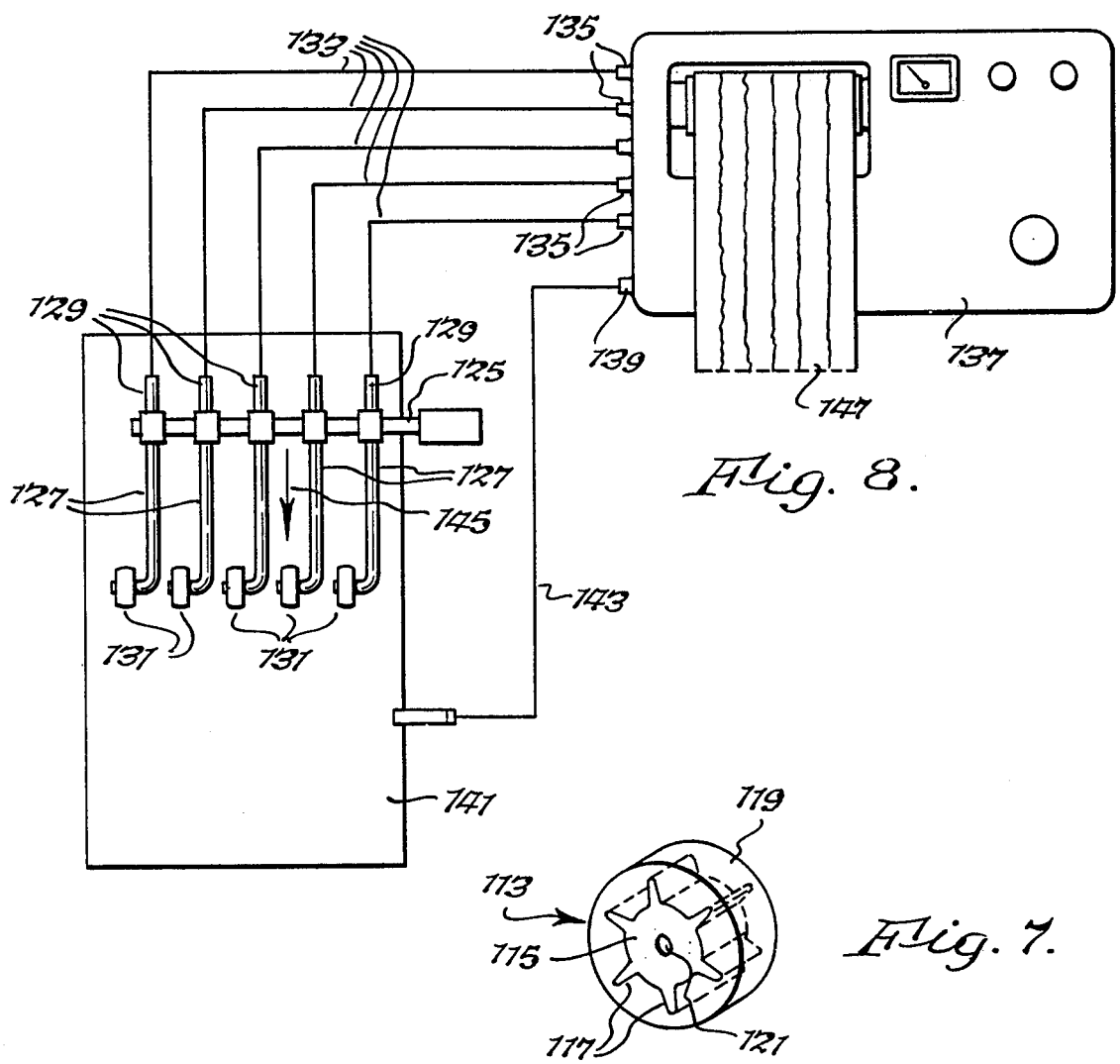

PROCESS FOR DETERMINING PROPERTIES OF MATERIALS

This application is in part a continuation of copending application Ser. No. 754,571, filed Dec. 27, 1976, now abandoned, which is a division of application Ser. No. 574,360, filed May 5, 1975 now U.S. Pat. No. 4,006,063, granted Feb. 1, 1977, which was a continuation of application Ser. No. 79,033, filed Oct. 8, 1970, now abandoned.

This invention is concerned with procedures for obtaining and measuring information encoded in electrically conductive products as a result of their manufacturing history as well as for the evaluation of such information and/or its presentation in some useful form, such as a matrix, which is a rectangular array of numbers and which may be defined in terms of one or more rows and/or columns. The reduction of a square matrix, for example, to its characteristic equation is straightforward and is of singular importance in physical theory.

The invention relates to methods of detecting and measuring and/or comparing chemical, physical, and/or mechanical characteristics and properties of such products under a variety of conditions, and with apparatus for performing such methods.

Although means exist for determining various chemical, physical, and mechanical properties of manufactured products either in the field or in the laboratory by either destructive or nondestructive methods, these means and their application can be limited by such factors as test specimen size and configuration, specimen preparation, and ambient or environmental conditions, as well as the type and quantity of the information provided and economic parameters which include time. Any material body can act as a carrier of information. For example, a standard weight carries the information implicit in the accuracy with which its mass is known.

An object of this invention is to provide data from which useful mathematical expressions may be derived which relate to some measure of the information content of an electrically conductive manufactured product determined in terms of its elemental constituents.

The total information content of a system can include but is not limited by the following: physicochemical variations related to internal composition, surface chemistry, and distribution of the relative internal stored energy, as well as its thermal, mechanical and environmental history. It is important and desirable to be able to determine and/or map out, the areas and the degree of differences involved.

Another object of this invention is to provide for obtaining a better understanding of the nature of certain electronic transistors that may occur on the surface or within the volume of a surface film or coating upon conductors and/or within such materials; and therefore a means of transferring information that has been encoded in a product as a result of its particular manufacture.

In carrying out the process of the present invention, advantage is taken of the phenomenon that when two electrodes are first placed in contact with an electrolyte, for example a solution of a metal salt, there is an electrical voltage generated between the electrodes even when both electrodes are of the same metal and the electrolyte is also a salt of that metal. The voltage generated between a product serving as an electrode and a test electrode through an electrolyte is hereinafter called a mechanogalvanic potential and is often referred to herein, for convenience, as an MGP. The MGP at any point on the surface of a produce (electrode) is influenced not only by surface chemistry, but also by stresses in the product and other physicochemical differences. Thus, the MPG is a reflection, from the vantage point of the surface being examined, of the total information content of the product encoded as a result of its manufacture.

Since differences in temperature of the electrodes, the amount of light falling thereon, and other factors which affect the conductivity of the system may cause voltage variations, it is important that in determining the mechanogalvanic potentials of a test specimen, so far as possible, the electrodes, i.e. the specimen being tested and the test electrode, are subjected to the same conditions. It is also important that the test electrodes are as free as possible from stresses and contamination or are standardized. Otherwise, the test results may not accurately reflect the true condition of the test specimen or product. Thus, in the following description, it will be understood without specific mention that ambient conditions during testing may be controlled for purposes of standardization. As hereinafter described, the mechanogalvanic potential of a specimen or product may also be determined using a test electrode which is not of the same material as the test specimen and/or an electrolyte which is not a compound of either the material of the test specimen or of the test electrode.

It is to be understood that while, in the previous applications mentioned above and hereinafter, reference is made to gelled solutions of electrolytes, in the present application electrolyte is given the broad meaning: a substance that conducts electricity by transfer of ions or other charged carriers. Thus, the term electrolyte includes, but is not necessarily limited to, certain salts of metal-like materials and chemical constituents thereof, both in solid form and in solution, metal oxides, and ceramic materials such as certain glasses. Electrolyte solutions may be either aqueous or non-aqueous.

In testing or characterizing products in accordance with the process of the present invention, a three component system is employed: (1) a product which acts as an electrode, either anode or cathode, (2) a test electrode of a conductive material, and (3) an electrolyte that is maintained in constant contact with both electrodes. As explained below, it has been found most satisfactory to roll the test electrode and the electrolyte over and in contact with the surface of the product, usually with the test electrode constituting the hub of a wheel and the electrolyte being carried thereon as a tire or rim so that, in use, it is in electrical contact with both electrodes.

The determination of variations in mechanogalvanic potential at points on the surface of an electrically conductive product can be made by measuring the MGP at a number of either random or ordered discrete points on such surface. It is clear, however, that much more information is obtainable, and a more manageable and complete characterization can be made, if the mechanogalvanic potentials are continually read along one or more lines from one end or side of the product to the other, preferably in a minimum of time. This is most conveniently and accurately done with a probe which comprises a test electrode and a rollable body containing an electrolyte, by rolling said body along a path or paths on the surface of the product while maintaining said electrode and said surface in electrical contact through said electrolyte and recording the voltage and the polarity of such voltage generated during said rolling.

Although the information obtainable about a product by the use of apparatus that scans one or more paths on the surface of the product to determine the mechanogalvanic potentials at successive points along such path or paths is helpful in making a characterization of the product, much more information is obtainable when the scanning is done with respect to a plurality of the constituent elements in the product. It is obvious, for example, that in most metals the distribution of alloying constituents is not uniform and it is known that different elements in a system are not uniformly and equally affected by physical or chemical processing. Hence, there is an advantage in scanning a product in terms of elemental constituents. The information obtained is derived from the product as a whole while including surface-related contributions. Therefore, by mapping the mechanogalvanic potentials over a product surface, one can obtain a reflection or index of the total information content of the system represented by the product. The obtaining of such system characterization is not limited by product dimensions, weight, volume, and geometry.

In terms of this invention, the product being examined or tested is considered an electronic continuum and the relative internal stored energy and its distribution within the continuum is an important consideration. No matter what part of the product is being examined, there are certain systems characteristics that are common and are revealed by mapping the product in terms of one or more of its elemental constituents. Thus, the invention allows determination of the location and extent of anomalies in the structure of a product, determination of the general overall physicochemical uniformity of the product system, and the obtaining of relative measures of the internal stored energy and its distribution in the system before, during and/or after the application of stress.

The invention of the present application makes possible such characterizations and thus further makes possible four important and immediate practical applications: (1) providing insight into constituent-systems relationships (a powerful research tool), (2) derivation of systems equations of state, (3) providing evolutionary feedback for product research and development, quality control, and cost effectiveness, and (4) the testing of entire product populations rather than merely testing samples thereof.

This invention further enables a rapid and economically favorable systems characterization in terms of the elemental constituents in the form of numerical and/or topographic mappings as well as providing matrices which are the mathematical basis for the derivation of various characteristic algebraic equations and/or other important mathematical quantities since physical phenomenon may best be understood when physical quantities are presented in a quantitative manner.

The present invention can be employed both in a plant and in the field and has application, for example, for testing storage and fluid transmission systems such as high pressure vessels for liquified natural gas and pipelines as well as products of any size, such as very large forgings and thin films.

FIG. 1 is a partially schematic view of apparatus for measuring and comparing the mechanogalvanic potentials at successive points along the surface of a product.

FIG. 2 is an enlarged, fragmentary view of the wave form obtained with the apparatus of FIG. 1;

FIG. 3 is a fragmentary side view of a probe with a rolling electrolyte carrier suitable for use in the apparatus illustrated in FIG. 1;

FIG. 4 is a sectional view on line 4—4 of the probe shown in FIG. 3;

FIG. 5 is a side view of another form of probe;

FIG. 6 is a sectional view on line 6—6 of the probe shown in FIG. 5;

FIG. 7 is a perspective view on another form of electrolyte carrier;

FIG. 8 is a schematic view similar to FIG. 1 but illustrating apparatus adapted to obtain a plurality of simultaneous continuous recordings of the mechanogalvanic potentials at different points on the surface of a product;

FIG. 1 illustrates schematically a form of apparatus suitable for reading continuously and recording the mechanogalvanic potentials along a path on the surface of a product.

Figure 9:
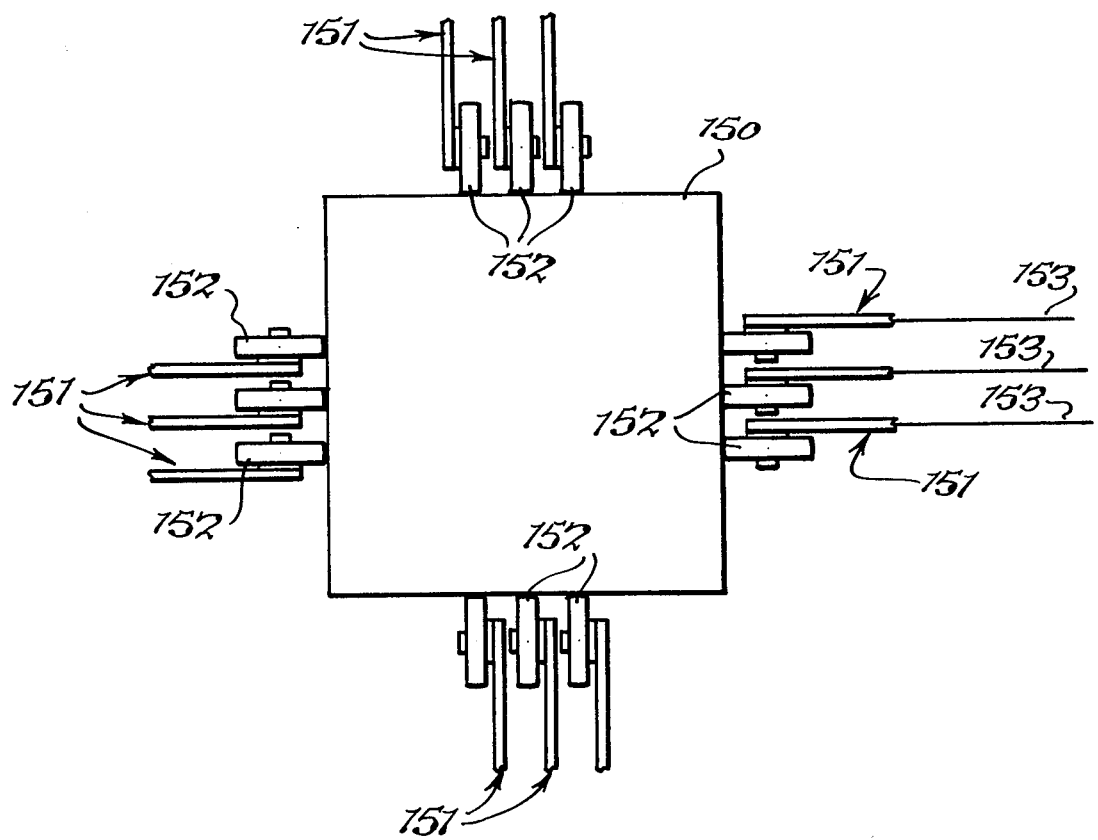
FIG. 9 is a schematic showing of the simultaneous scanning, with a plurality of probes, of a plurality of surfaces of a product.

In FIG. 1 a metal plate 61 having a weld joint 63 is electrically connected by a suitably attached lead 65 to one terminal of a recording voltmeter 67. The other terminal of the voltmeter is electrically connected by lead 69 to the electrode of a wheel-type test probe comprehensively designated 71. The probe 71 comprises an insulating handle 73 and a wheel 75 which contains a test electrode and serves as an electrolyte carrier. The wheel is rotatably mounted on a metal rod 77. The construction and mounting of the wheel 75 is hereinafter described more specifically. Suffice it here to say that the circumferential surface of the wheel carries an electrolyte, for example as a tire of gelled electrolyte solution, so that in use the electrolyte is maintained between and in contact with the test electrode and the surface of the specimen or product.

When rolling the wheel 75 over the surface of the product 61 the recording voltmeter 67 produces a permanent record on the tape 79 of the mechanogalvanic potentials along the line, indicated at 81, followed by the wheel. FIG. 2 shows, enlarged, a portion of the tape 79 with the recorded mechanogalvanic potentials being depicted by the line 83.

In carrying out tests with a rolling electrolyte carrier and a recording voltmeter the recording pen of the meter is initially adjusted to the O voltage line of the recording chart or tape. As shown by the line 83 on the tape 79, when the wheel rolls over the surface of the product a potential is generated and recorded. The wave form, line 83, also illustrates the deviation from a average base line signal that occurs as physicochemical conditions in or on the product result in variations in the MGP. Such deviations may be so great as to cause a reversal of polarity in the MGP, the tape 79 illustrating such a reversal in the area of the weld 63 on the product or specimen. It will be understood that the wheel 75 may be run repeatedly over the surface of the product 61 in parallel lines in any direction or in a pattern, the accumulated readings of mechanogalvanic potentials permitting accurate plotting or mapping of information derived from the product.

A large number of materials and styles of construction may be used in forming rollable electrolyte carriers for test probes, according to the invention. In FIGS. 3 and 4 a very simple form is illustrated in which a metal electrode 87, having an insulating handle 89, is provided at one end with an angled, reduced portion 91 which serves as an axle for the wheel 93, the other end (not shown) of the electrode being provided with suitable means for attachment of an electrical lead. The wheel 93 carries electrolyte solution and is rotatable on the angled portion 91 of the electrode which extends through an axial bore in the wheel. Suitable means such, for example, as an enlarged portion 95 on the extremity of the axle portion may serve to hold the wheel 93 in place.

The construction of wheel 93 may vary greatly, as desired. It may, for example, be constructed of fabric, either felted or woven, paper, wood, natural or synthetic sponge, or porous ceramics, in all cases being substantially saturated, when in use, with an appropriate electrolyte. In many cases, a gelled electrolyte solution, such as hereinafter described, is preferred, the gelled electrolyte solution being cast or otherwise formed into a wheel of desired size and cross-sectional configuration. It will be evident that as the wheel 93 is rolled along the product surface, represented at 97 in FIG. 3, the electrolyte therein is in contact with both the product and the test electrode.

FIGS. 5 and 6 depict another form of electrolyte carrier for test probes in which a metal core or hub 101 is provided with an annular tire or rim 103 of electrolyte-carrying material. Such material may be any of those previously mentioned but, often, tires of gelled electrolyte solution are preferred, the gel being readily molded on the core. The carrier is rotatably mounted on an axle 105 provided on one end of the metal shaft 107. The latter is provided at its other end (not shown) with suitable means for connection of an electrical lead thereto and is also provided with an insulating coating or handle (not shown) for grasping or mounting. The axle 105 passes through and is in electrical contact with the hub 101 and the latter, which serves as the test electrode for the probe, is conveniently held on the axle, against the shoulder 109 of the shaft 107 by a removable retaining ring 111.

It will be understood that the test electrode 101 need not be of a single material. Thus the hub may comprise an inner portion of an inexpensive, conducting material such as copper and an outer portion, in contact with the tire, of a more expensive material such as platinum, the two portions of the hub being in good electrical contact and formed into a composite body by cladding, plating or in other suitable manner. The same holds true for the portion of the electrode 87, described above. The portion thereof on which the wheel 93 is mounted may be of material different from the remainder of the electrode.

FIG. 7 illustrates a modification of the electrolyte carrier shown in FIGS. 5 and 6. In this modified carrier 113 the metal test electrode, i.e. hub or core 115, is provided with radially projecting fins or webs 117 which serve to hold and support an electrolyte-containing outer portion or rim 119, which may be molded thereon. The wheel 113 may be mounted for rotation on a conducting electrode holder by the axial bore 121 through the hub electrode, in the same manner as the wheel illustrated in FIGS. 5 and 6. The rim 119 may be formed of any suitable porous material such as one of those described above. However, a gelled electrolyte solution is often preferred.

Electrode-containing wheels such as are shown in FIGS. 5–7, inclusive, having a tire or rim of gelled electrolyte solution on a conductive, e.g. metal, core or hub which serves as an electrode, can be easily produced. In application Ser. No. 574,360, above-referred to, the manufacture of such wheels is described.

When the mechanogalvanic potentials over a large surface are to be mapped, many determinations or readings must be taken. In FIG. 8 means is shown for scanning a specimen or product by simultaneously making a plurality of MGP readings along parallel lines across the surface thereof. As there illustrated somewhat schematically, a cross-bar or rod 125, which is suitably mounted, e.g. on a carriage (not shown) if operation is to be mechanized or automated, carries a plurality of probes 127. These are spaced longitudinally on the rod 125, on which they may be adjustably held, for example, by sliding clamps 129. The probes 127 preferably include electrolyte-carrying wheels 131 like, for example, any of those shown in FIGS. 5–7, but which may be of other suitable designs. The electrodes in the several probes are insulated from each other by suitable means and are electrically connected by leads 133 to suitable terminals 135 on a multi-channel, recording voltmeter 137. An electrical connection from the terminal 139 of the latter to the product 141, the surface of which is to be mapped, is provided by the lead 143. Thus, as the electrode carriers 131 are rolled along the surface of the specimen, as indicated by the arrow 145, an individual record will be provided on the tape or chart 147 of the mechanogalvanic potential at successive points along the path followed by each wheel.

It will be understood that apparatus such as shown in FIG. 8 may be provided with any desired number of probes, each having a rollable electrode carrier, which may be spaced at any desired distances. If necessary, of course, more than one recording device may be used. Further, while a plurality of electrolyte-carrying wheels may be manually moved over a surface by the cross bar or rod 125, either the product and/or the assembly of mounted wheels may be mounted on a suitably powered carriage and may be moved with reference to the other, thereby permitting automation of the mapping. It will be understood that any or all of the probes and/or the rollable electrolyte carriers thereon may be replaced with identical or different ones.

As indicated above, the present invention is concerned with characterizing the class of electrically conductive products. Representative of such class are products made of metals, including alloys and composites having metal matrices, of materials such as those variously referred to as semiconductors or metalloids, for example germanium, carbon, silicon, galina and boron, and of biological products.

For test electrodes any member of the above-mentioned class of electrically conductive products may be used. In general, it is desirable to employ a rollable electrolyte carrier having a conductive hub (test electrode) in which at least the portion thereof in contact with the electrolyte is formed of a material containing one of the elements to be found in the article being scanned. Test electrodes should also be as free from internal stress and surface contamination as practical. However, small differences in composition are not usually important. Indeed, it has been found convenient in many cases to use as a test electrode, in determining the MGP of various conductive products, a chemically resistive metal such, for example, as platinum, gold, palladium, and tantalum, as well as carbon, preferably as graphite. On the other hand, any conductive material may serve, with a suitable electrolyte, as a test electrode.

As above stated, the present process may be employed in testing products formed of alloys. This may be done by the use of multiple test electrodes and electrolytes. Thus, for example, in testing a product formed of a copper-tin alloy, such as bronze, the product surface may be scanned with a probe using a copper test electrode and a gelled solution of a copper salt as the electrolyte, and then scanned again with a probe using a tin electrode and a gelled tin salt solution electrolyte. The two sets of readings, each of which provides definitive information may then be compared. In most cases it will be convenient and time saving in testing alloy products to use apparatus in which a number of probes with rollable electrolyte carriers are simultaneously caused to roll across and in contact with the product. For example, use may be made of apparatus such as shown in FIG. 8 to scan a large surface quickly. This can be done according to one procedure by having in each scan, all of the test electrodes of the same material and all of the electrolytes of the same material but different from that of the electrodes and, in successive scans, using electrodes and/or electrolytes of another material. This repeated scanning can be continued until the alloy product has been scanned for each of the elemental constituents thereof, or as many of them as is desired. Alternatively, each of the probes may have a different test electrode and electrolyte so that only one complete scanning of a large surface will suffice to obtain the desired information. FIGS. 9–12 also show, schematically, arrangements of multiple probes adapted for scanning large surfaces conveniently and quickly. It will be understood that the probes shown in each of these figures may be of any desired and suitable construction and materials, and that suitable electrical connections will be made to permit recording of the mechanogalvanic potentials along the paths traced by each of the probes.

In FIG. 9 there is schematically shown apparatus which permits simultaneous scanning of an electrically conductive product from different vantage points. As illustrated, a plurality of test probes 151 are so arranged as to be rolled along each side of the specimen 150, the latter being viewed from an end. Each of the probes comprises a rollable body 152, consisting of or comprising an electrolyte, and a test electrode. Said body may be formed of a test electrode hub and an electrolyte tire, as shown in FIG. 5 or FIG. 7 or may be a solid electrolyte as shown in FIG. 4. Suitable electrical connections, such as leads 153 are made to the test electrode for connection with a suitable data-processing system (not shown) and another direct electrical connection (not shown) is provided between the product 150 and the system. This is substantially similar to the set-up illustrated in FIG. 8. The several probes in each group can be of any desired construction and are suitably mounted, e.g. on a common support (not shown), and either the product or one or more of such groups can be mounted on a suitable movable carriage (not shown). As in the apparatus shown in FIG. 8, all of the probes in each group of probes may have test electrodes of the same material and electrolytes of the same material. However, one or more of the probes in each group may have a test electrode and/or electrolyte which is different from that in the other probes of said group. Also, of course, the one or more of the probes in one of said groups may be different from the probes in another of said groups.

Figure 10:
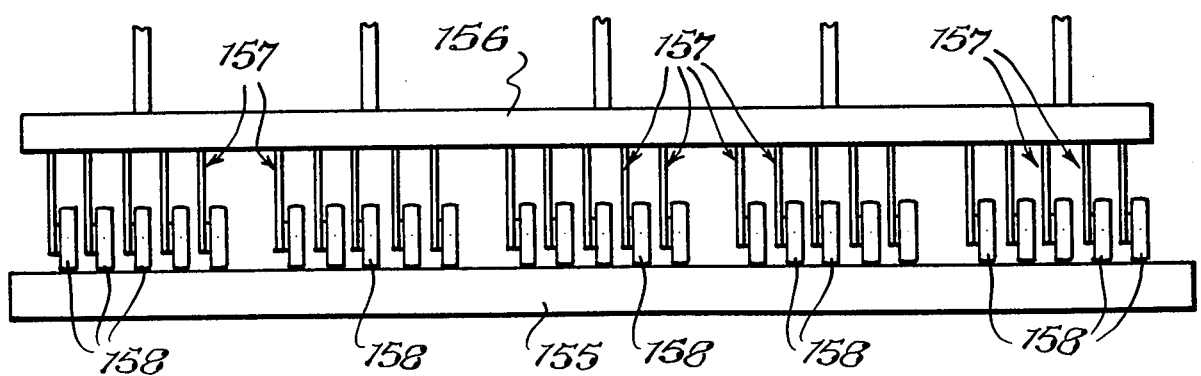
FIG. 10 is a schematic view showing an arrangement for simultaneously scanning a large surface with a plurality of groups of probes.

FIG. 10 illustrates, schematically, apparatus for the simultaneous scanning of a large surface. The electrically conductive specimen 155, shown from an end, is a large plate or slab and there is provided a suitable support 156 on which there is mounted a plurality of groups of test probes 157. As in FIG. 9, each of the probes comprises a rollable body 158, consisting of or comprising an electrolyte, and a test electrode. As in FIGS. 5 and 7 said body may be formed of a test electrode hub and an electrolyte tire, or it may be a solid electrolyte as in FIG. 4. Also as in the apparatus shown in FIG. 9, suitable electrical connections (not shown) are made between the product and each of the test electrodes with a suitable data processing system (not shown). The support 156 is carried by suitable fixed or movable means (not shown). As in the apparatus shown in FIG. 9, the materials of the test electrode and of the electrolyte in each of the several probes may be varied.

Figure 11:
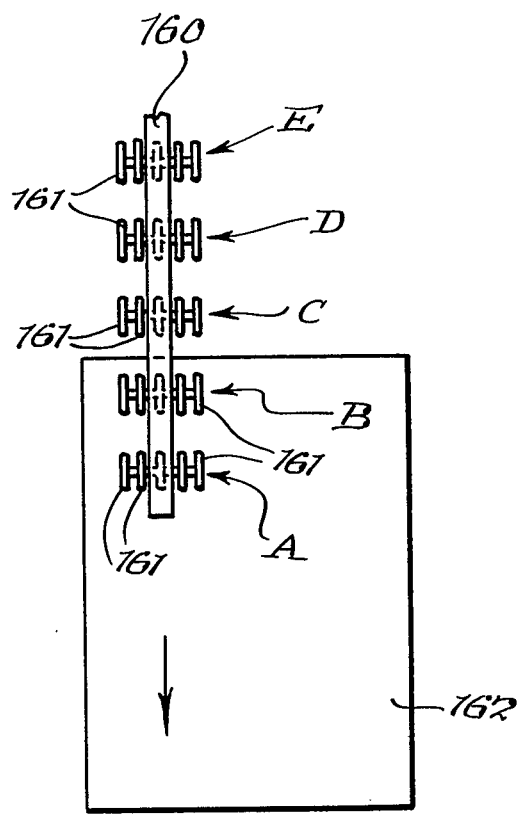
FIGS. 11 and 12 are schematic views showing other multiprobe arrangements.
Figure 12:
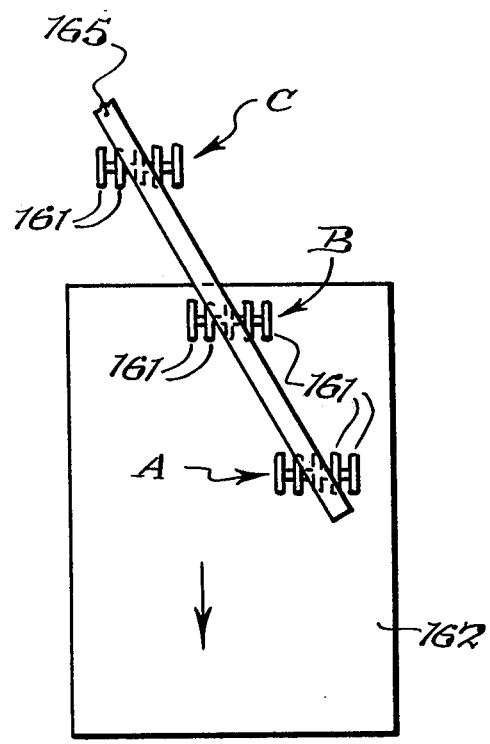

FIGS. 11 and 12 are schematic illustrations of additional possible arrangements of multiple probes for scanning the surfaces of electrically conductive products. In FIG. 11 a carriage 160 supports and carries a plurality of groups of probes 161 in longitudinal alignment. Each probe, shown symbolically merely as a wheel, has a construction like that of the probes 151 and 157 described above and in each of the aligned groups A-E each probe is adapted for independent connection with a suitable data processing system (not shown) to permit recording of the mechanogalvanic potentials along the path of its movement on the surface of the product 162. Such an arrangement of probes is particularly useful in scanning a relatively large product in terms of a number of elemental constituents since in each of the groups the several probes can be the same, i.e. with test electrodes of the same material and the same electrolyte, but with the probes in each of the successive groups having test electrodes and/or electrolytes different from those in the other groups. Thus, for example, the probes in group A could have iron electrodes, those in group B could have manganese electrodes, those in group C could have silicon electrodes, those in group D, carbon electrodes, and those in group E could have molybdenum electrodes, with suitable electrolytes used in the probes of each group. This would permit rapid scanning of large surfaces for a plurality of elements.

FIG. 12 shows a variation of the apparatus shown in FIG. 11 in which the groups A, B, and C of probes 161 are supported by the carriage 165 in staggered relation instead of longitudinally aligned. It will be understood that the carriages 160 and 161 may be attached to any desired fixed or movable support (not shown), groups of probes may be added to or removed therefrom, and that the probes may be attached to the carriages in any desired manner. It will also be understood that in the apparatus of FIGS. 11 and 12 as well as that of FIGS. 9 and 10 the number of groups of probes can be varied as desired and each group can comprise as many probes as are desired or feasible.

The process of the present invention is capable of extensive use. Information as to the stressed condition of the product system so that the results of heat treatment, annealing, normalizing and the like can be studied, or welded areas be evaluated, e.g. in preparation for metal processing. Information as to the physicochemical uniformity of the system can also be obtained by mapping the mechanogalvanic potentials of an electrically conductive product. Thus, differences in uniformity of surface treatment can be determined and areas can be located and defined which have different chemical compositions or which contain impurities, such as corrosion products, or which have been contaminated. Not only can bars, plates, and sheets be characterized by the present invention, but also larger or smaller bodies, such as ingots, slabs and castings as well as wire and thin films. It is also possible to employ the present invention on the same product before and/or after and/or during stressing of the body, for example, by bending a sheet or tensioning a spring. This permits the acquiring of information which may be helpful in ascertaining the onset or development of fatigue and ultimate mechanical failure of the body. Tests may be carried out on either hot or cold and on both polished and unpolished bodies.

Figure 13:
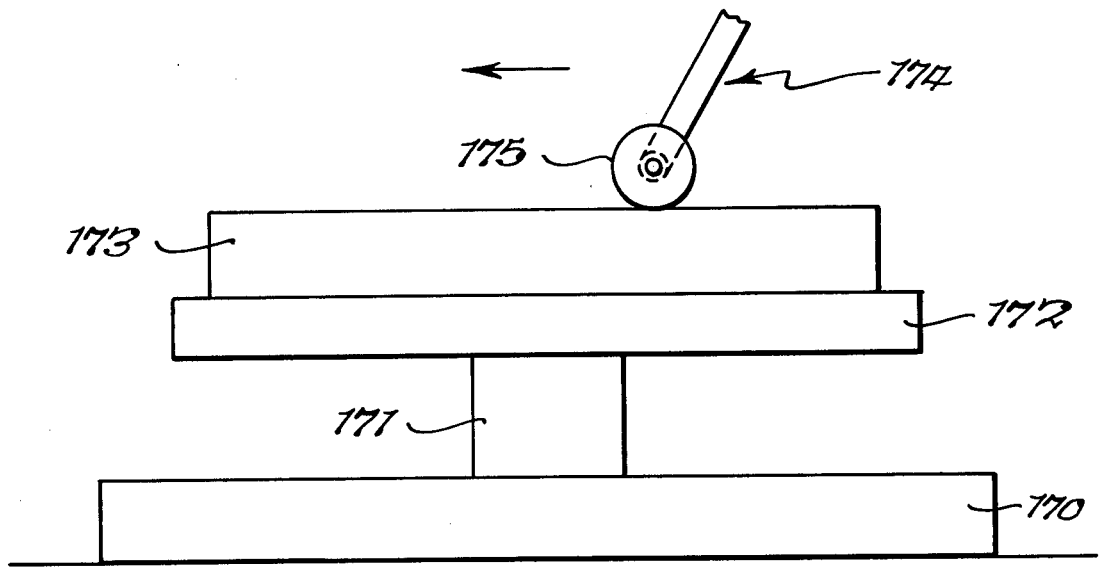
FIG. 13 is a schematic view illustrating the scanning of a surface of a product during stressing.

FIG. 13 shows schematically apparatus for scanning an electrically conductive product under vibrational stress. As shown, the base 170 of the apparatus supports a transducer 171 to which suitable electrical connections (not shown) are made for producing vibration therefrom. The transducer has mounted thereon a table 172 on which the product, illustrated as a bar 173, is laid. A probe 174 comprising a rollable body 175, consisting of or comprising an electrolyte, and a test electrode, such as is shown in FIG. 4 or 6, is provided for scanning the product, suitable electrical connections (not shown) being made between the test electrode, the product, and a recording device (not shown). It will be understood that the single probe 174 shown may be replaced by a multiplicity of probes in, for example, an arrangement such as is shown in FIG. 8, and that the product may be scanned for a plurality of its constituent elements, as described above, when desired. It will further be understood that the specimen can also be scanned before and/or after the application of the vibration so that the effects of the vibration can be determined. The intensity and frequency of the vibration employed can be varied as desired.

Figure 14A:
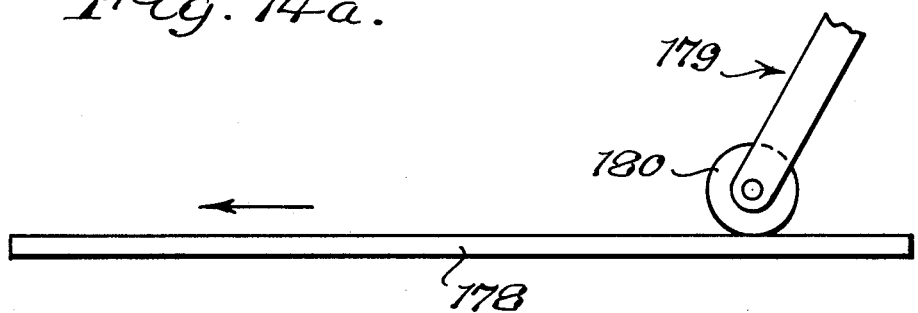
FIG. 14a is a schematic view showing the scanning of a product before bending.
Figure 14B:
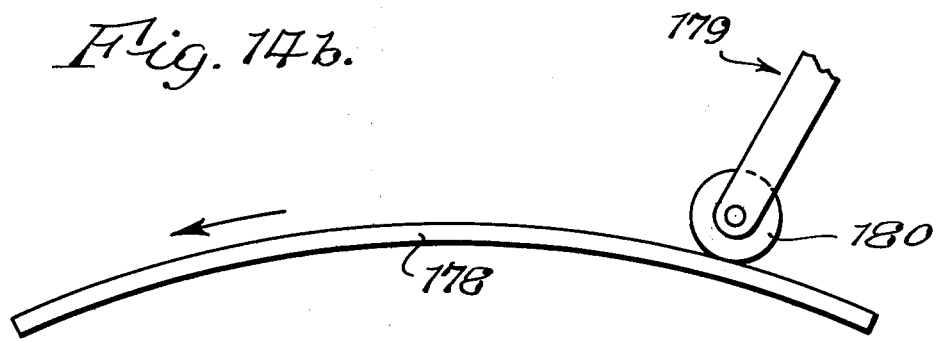
FIG. 14b is a view similar to FIG. 14a showing the scanning of the same product after bending.

FIGS. 14a and 14b illustrate schematically the scanning of electrically conductive products subjected to bending stress. As shown in FIG. 14a, a product in the form of a plate 178 is scanned before bending, usually a probe 179 having a rollable body 180, consisting of or comprising an electrolyte, and a test electrode, such as is shown in FIG. 4 or 6. FIG. 14b illustrates a similar scanning of the product 178 after application of such force as to permanently deform the specimen. Comparisons of the mappings of the mechanogalvanic potentials obtained in the successive scannings in such cases have shown marked differences and it has been found that usually such differences are much greater with respect to certain of the elemental constituents of the product than with respect to others, as hereinafter set forth. Consequently, it is usually desirable to scan the product in such a way that the effect of the stress on a plurality of the elemental constituents of the product is determined. This can be done by repeatedly scanning the product, both before and after bending, with a single probe as shown, each scan being performed with a different test electrode and/or electrolyte, or by employing apparatus having a multiplicity of probes, each with a different test electrode and/or electrolyte. It will also be understood that, if desired, scanning may be carried out during deformation and/or after restoration of the product to its original state.

It has been found that often all elemental constituents in a product do not react in the same manner to a force or stress applied to the product. Frequently one elemental constituent is found to have a relatively greater change in MGP in response to the action of the force than other constituents. Such an element may be termed a "detector element" and its action may be referred to as "chemical amplification". Where a detector element can be experimentally determined for a type of material it makes use of the present invention for such a purpose as quality control much more convenient and inexpensive.

There are described below details of several examples of scanning in terms of the elemental constituents of a product.

EXAMPLE 1

Four heat-treated specimens of 309 stainless steel were tested by repeated scanning thereof. Each specimen was scanned with a wheel having a high-purity iron electrode carrying and in contact with a tire of a gelled solution of ferrous sulfate as electrolyte. Similar scans on each specimen were carried out successively with a nickel electrode and gelled nickelous sulfate solution, with a chromium electrode and gelled $Cr_2(SO_4)_3$ solution, and with a graphite electrode and a gelled solution of sodium chloride as electrolyte. There were thus obtained separate scans of each specimen for four of the constituent elements, iron, nickel, chromium, and carbon. In comparing the mappings of the mechanogalvanic potentials for each of these elements, it was found that with each of the four specimens the mappings for chromium were significantly different and permitted the arrangement of the specimens in the order of the severity of the heat treatment employed since the amount of chromium carbide precipitation is known to be affected by heat treating.

EXAMPLE 2

Two specimens of a niobium-tin ($Nb_3Sn$) alloy superconducting wire, each having a diameter of approximately 0.0002 mm, were tested. Two longitudinal scans were made on each specimen, 180° apart, by a probe having a test electrode of tin and a gelled electrolyte comprising a solution of stannous sulfate and the scanning was repeated with a probe in which the test electrode was high-purity niobium and the gelled electrolyte was a water solution of the reaction product of $Nb_2O_5$ with sulfuric acid.

When the MGP data obtained from both scans of both wires were plotted on chart paper, it was found that although neither wire specimen was uniform throughout its length, one specimen was much less uniform than the other.

EXAMPLE 3

An ingot of vacuum cast, high alloy steel containing as alloy constituents, in addition to iron and carbon nickel, cobalt, chromium, and molybdenum was scanned circumferentially at spaced intervals. Successive scans were made with probes using (1) a test electrode of high purity iron and a gelled ferrous sulfate electrolyte, (2) a test electrode of nickel and a gelled nickelous sulfate electrolyte, (3) a test electrode of cobalt and a gelled cobaltous sulfate electrolyte, (4) a test electrode of chromium and a gelled $Cr_2(SO_4)_3$ electrolyte, (5) a test electrode of molybdenum and a gelled molybdic acid electrolyte, and (6) a test electrode of graphite and a gelled sodium chloride electrolyte. A mapping was made from the MGP readings obtained by the several scans with respect to each of the elements. Comparisons of these mappings revealed a considerable degree of physicochemical non-uniformity in elemental distribution or state and defined the areas of non-uniformity.

EXAMPLE 4

A sheet, approximately 13 cm × 4 cm × 0.04 cm in size, of 55-NITINOL (a mechanical memory alloy) was scanned top and bottom using successively a nickel test electrode with a gelled nickelous sulfate solution as electrolyte and a titanium test electrode. With the latter as an electrolyte there was used a gel of the reaction product of $TiO_2$ with sulfuric acid. Mapping of the mechanogalvanic potentials determined by the scanning showed that the physicochemical characteristics of the sheet were non-uniform.

EXAMPLE 5

A small plate of 309 stainless steel 1.335 mm thick, and approximately 2.5 cm × 45.7 cm in width and length, respectively, was given 26 stress cycles which involved bending it across its width, alternately through 90° in opposite directions, by means of conventional bending apparatus. Using test electrodes and electrolytes identical to those described above in Example 1, the specimen was scanned for each of the elements Fe, Cr, Ni and C, initially and after each stress cycle. It was found that the average MGP of chromium declined rapidly, a polarity change therein occurring after only three of the stress cycles. Although the constituents Fe, Ni, and C showed variations in their average respective MGP readings during the test, these variations were nowhere near so great as those occurring with chromium and there were no other changes in polarity of the voltages. At the conclusion of the 26th cycle, the average chromium MGP had declined from 240 mV to −90 mV. The chromium was clearly acting as a "detector element" of the type referred to above. It was apparent at that time that mechanical failure of the specimen would occur during the next bending cycle. It is, therefore, evident that scannings made on a mechanical element or part that is subject to bending stress in use can be used to predict imminent mechanical failure of the part or element and/or quantitatively measure fatigue.

EXAMPLE 6

A plate of alloy steel approximately 61 cm × 30.5 cm × 1.3 cm was scanned for Fe, C, P, Si, and Mn using test electrodes, respectively, of iron, carbon, high phosphorus steel, silicon, manganese with, respectively, gelled solutions of ferrous sulfate, sodium chloride, phosphoric acid, sodium silicate and manganous sulfate as electrolytes. The product was also scanned using a platinum test electrode and a gelled platinic chloride solution as electrolyte. Mappings were made from the mechanogalvanic potentials determined in the scannings.

Thereafter, using apparatus similar to that illustrated in FIG. 13, the plate was subjected to vibration (60 Hz) and while so subjected was again scanned and mapped as described above.

It was found that the elemental constituents of the plate were affected differently by the vibration and that physicochemical anomalies were revealed under vibration that were not revealed previously.

It will be evident that scanning can also be carried out before and/or after vibration to ascertain the permanent effect, if any, of the stress of vibration. Also, of course, repeated scanning at intervals after vibration can be performed to ascertain the relaxation time required for recovery from the effects thereof.

Stresses can also be applied to products by the application of or withdrawal of heat therefrom. Apparatus for such application or withdrawal is shown schematically in FIG. 15. In that figure the product 185 is supported on refractory, and preferably insulating, blocks 186. It may be heated in any suitable manner. For example, it may be heated in a furnace (not shown) and then placed on the supporting blocks. Alternatively, it may be heated by high frequency induction heating. Other heating means can also be used, if desired. The probe 187 which may be used in scanning the heated product has a rollable body 189, which consists of or comprises an electrolyte and a test electrode, such as is shown in FIG. 4 or 6. Of course, when scanning in terms of elemental constituents of the sample, it is more convenient to employ a plurality of probes and repeatedly scan with probes in which the test electrodes and/or the electrolytes are different.

Figure 15:
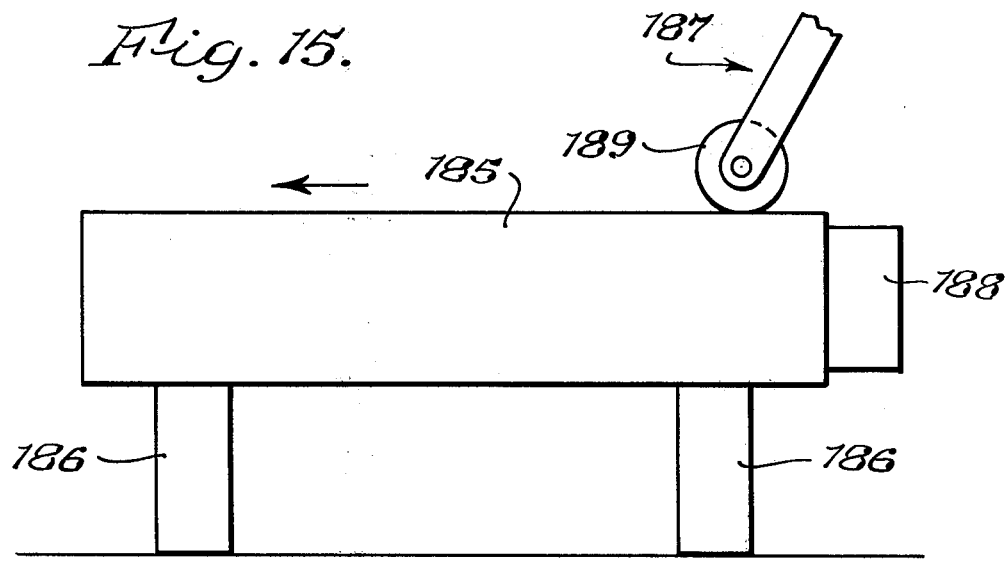
FIG. 15 is a schematic view illustrating the scanning of the surface of a product during heating or cooling.

A similar procedure can be used in scanning a cold product, the product being previously cooled or being cooled after mounting on the blocks 186. In FIG. 15, the numeral 188 designates schematically a suitable device for heating or cooling the product which can be used in studying the effect of heat flow through the sample. Thus, when 188 is a heating device, repeated scanning of the sample 185 while heat is supplied to one end thereof by the device 188 will reveal the effect of the heat wave passing through the sample on anomalies in the structure or composition of the sample. A similar effect may be secured by cooling the product by the device 188.

Figure 18:
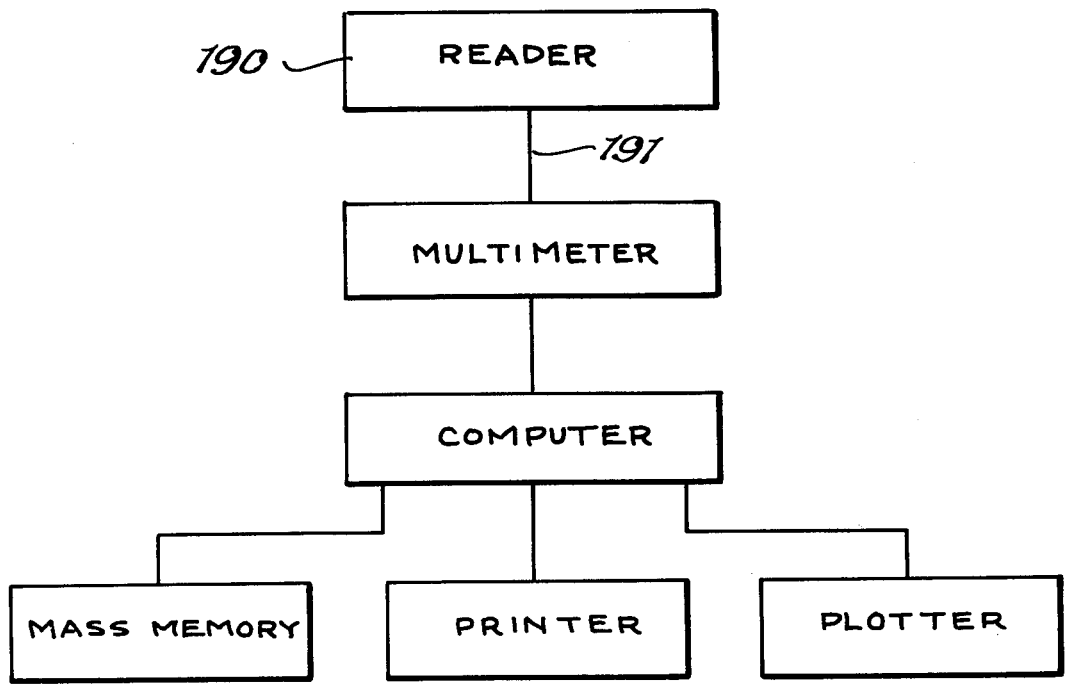
FIG. 18 is a diagram illustrating the relationship of apparatus useful for scanning products and processing the data obtained by such scanning.

In FIG. 18 there is presented a schematic layout of apparatus suitable for carrying out processes according to the present invention. The reader 190 is a scanning device. As explained above, this may be a simple probe consisting of a wheel having a suitable gelled electrolyte tire and a test electrode, e.g. a hub of desired material. On the other hand, it may be a multiple probe device such as is illustrated in FIGS. 8, 9, 10, 11 or 12.

The mechanogalvanic potentials generated by the probe or probes of the reader in passing over the product surface are fed by a suitable electrical cable 191 to substantially conventional data processing apparatus comprising a multichannel multimeter, mass memory, printer, plotter and a computer which interacts with and controls the other said devices. Such data processing apparati, operating with suitable programs, are obtainable on the market and are widely used in processing emf measurements.

The apparatus illustrated schematically in FIG. 18 permits great freedom in operations with data from the reader 190 and permits easy generation of elemental matrices that represent the variation of the MGP over the product surface, as well as the drawing of maps showing such variations, including topographic maps and three-dimensional perspectives, or so-called fishnet maps thereof with the Z-values representing the elemental mechanogalvanic potentials at the several (x, y) locations.

Figure 16:
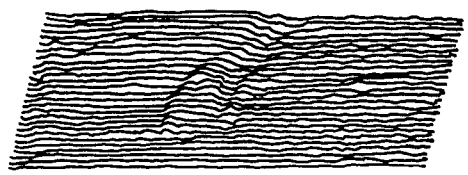
FIG. 16 is a representation of a fishnet map such as might be obtained by plotting the mechanogalvanic potentials over a product surface.
Figure 17:
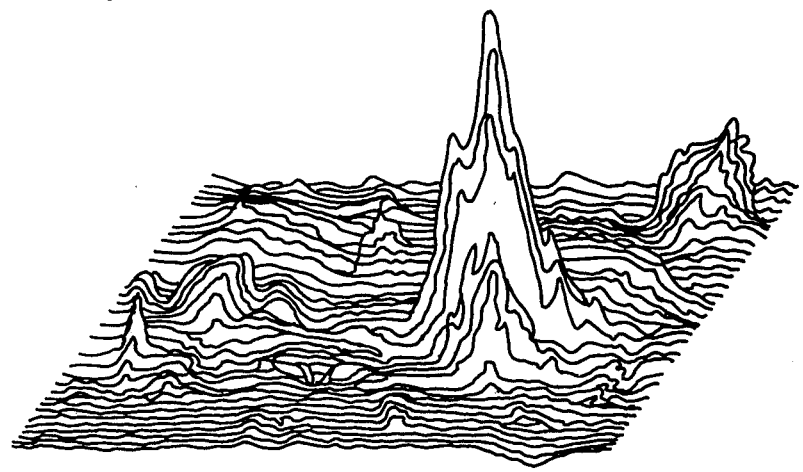
FIG. 17 is a representation of another fishnet map such as might be obtained by plotting the mechanogalvanic potentials over the same product surface after subjecting the specimen to stress.

FIGS. 16 and 17 are representations of typical fishnet maps such as might be obtained from a plotter. The map in FIG. 16 is relatively uniform, but shows an anomaly in the test product indicated by the ridges in the map. In contrast, in FIG. 17 the map is indicative of gross nonuniformity in the product.

A scan, as used herein, is the continuous generation of positive and/or negative mechanogalvanic potentials in a system in which a first electrode and a second electrode are in electrical contact through a solid electrolyte, by rolling over one or more paths on a surface of said first electrode a rollable element which consists of or comprises said electrolyte.

Scanning, as used herein, is the act of making one or more scans.

An electronic transition, as used herein, is the changing, either partially or completely, of the valence, the form of chemical bonding, and/or the mode of electrical conduction of one or more elemental constituents in an electrically conductive product.

It will be understood that the variety of test electrodes and electrolytes usable in accordance with the present invention is very wide. In addition to those mentioned above, test electrodes of, for example, lead sulfide, cuprous oxide and many metals and metal-like materials such as silicon, boron, germanium, silver, titanium, tungsten, beryllium, and magnesium. The electrolyte used may be a gel of an aqueous solution or of a suitable non-aqueous solution, for example a solution in a solvent such as propylene, carbonate, dimethylformamide, acetonitrile, dimethyl sulfoxide, and N,N-dimethylformamide. Such gels, when in the form of a wheel or a tire in conjunction with a test electrode are regarded as solid. Other solid electrolytes that have been used in carrying out the invention are silver bromide, electrically conductive resins, and an iron oxide layer produced on the rim of an iron wheel. Obviously, many other materials can be used either as test electrodes or as electrolytes. Since the processes of the present invention are comparative, the purity of the test electrodes and/or electrolytes used may not be critical. However, for very complete characterizations of a product it is desirable for the test electrodes not only to be identical in chemical composition, but also in phases and physical states.

In many cases, to obtain a more useful systems analysis, a composite map may be produced by recording in a single mapping the cumulative data derived from a series of equivalent elemental constituent scans of a product.

It has been set forth above that the relaxation time of a specimen or sample subjected to vibration can be determined by repeated elemental scanning at intervals after the vibration. The relaxation time of a specimen or sample subjected to the effect of other forces or stresses may also be determined by repeated elemental scanning after the stress or force is removed.

It will be understood that stress can be imposed on a product or specimen not only by the action of mechanical forces, but also by other phenomena, such as magnetic fields and electromagnetic radiation, that produce a change in the product.

It has been found that once a representative number of members of a product population of a conductive product have been properly characterized as to mechanical properties, other members of the same population can have their mechanical properties predicted by the type of nondestructive testing provided by the present invention.

It will be evident from the foregoing specification that certain electronic transitions that may occur on or within a conductive product may be much better understood by mapping such a product in terms of its elemental mechanogalvanic potentials and that the processes of the invention allow very great practical advances in non-destructive testing and important results therefrom.

I claim:

1. A process for measuring information encoded in a manufactured, electrically conductive product in which said product serves as an electrode in a system which includes a solid electrolyte and a second electrode which comprises the steps of repeatedly scanning said product by use of a second electrode and a rollable member which comprises a solid electrolyte, in each of which scans the material of at least one of said second electrode and said electrolyte is different, and recording the mechanogalvanic potentials at selected points along the paths of the scans.

2. A process as set forth in claim 1 in which the electrolyte used in carrying out each of said scans is a compound of one of the constituent elements of said product.

3. A process as set forth in claim 1 in which said second electrode is formed of one of the constituent elements of said product.

4. A process as set forth in claim 3 in which the electrolyte used in carrying out each of said scans is a compound of the material of said second electrode.

5. A process as set forth in claim 1 in which a plurality of second electrodes is used in carrying out each of said scans, each of said second electrodes being employed on a different portion of said product surface and each being formed of a different material.

6. A process as set forth in claim 1 in which, in each of successive scans of a surface area of said product, the second electrode is formed of different material.

7. A process for measuring information encoded in a manufactured, electrically conductive product in which said product serves as an electrode in a system which includes a solid electrolyte and a second electrode which comprises the steps of repeatedly scanning said product by use of a second electrode and a member rotatable thereon which comprises a solid electrolyte, in each of which scans the material of at least one of said second electrode and said electrolyte is different, and recording the mechanogalvanic potentials at selected points along the paths of the scans.

8. A process for determining the effect of stress on a manufactured, electrically conductive product which comprises: before application of said stress, obtaining a set of mechanogalvanic potentials characteristic of each of a plurality of constituent elements in said product, recording said potentials and, after application of said stress, obtaining another set of such mechanogalvanic potentials and recording said potentials.

9. A process as set forth in claim 8 in which said other set of potentials is obtained and recorded while said stress is being applied.

10. A process as set forth in claim 9 in which said stress is produced by inducing vibration in said product.

11. A process as set forth in claim 9 in which said stress in said product is induced by the action of mechanical force.

12. A process as set forth in claim 9 in which said stress in said product is induced by the action of electromagnetic radiation.

13. A process as set forth in claim 8 in which said stress is discontinued before said other set of potentials is obtained and recorded.

14. A process as set forth in claim 13 in which said stress is produced by inducing vibration in said product.

15. A process as set forth in claim 13 in which said stress in said product is induced by the action of mechanical force.

16. A process as set forth in claim 13 in which said stress in said product is induced by the action of electromagnetic radiation.

17. A process as set forth in claim 8 in which said stress is produced by inducing vibration in said product.

18. A process as set forth in claim 8 in which said stress in said product is induced by the action of mechanical force.

19. A process as set forth in claim 8 in which said stress in said product is induced by the action of electromagnetic radiation.

20. A process as set forth in claim 8 in which repeated applications of stress on said product are made and each said application is followed by the obtaining of another set of said mechanogalvanic potentials and in which said sets of potentials are compared, whereby to permit prediction of failure of said product from cumulative fatigue.

21. A process for determining the effect of a change of temperature on a manufactured, electrically conductive product which comprises: obtaining a set of mechanogalvanic potentials characteristic of each of a plurality of constituent elements in said product, recording said potentials, and thereafter obtaining and recording another set of said mechanogalvanic potentials after changing the temperature of said product.

22. A process as set forth in claim 21 in which said other set of potentials is obtained and recorded while the temperature of said product is changing.

23. A process as set forth in claim 22 in which said product is under stress during the obtaining of one set of said potentials.

24. A process as set forth in claim 21 in which said other set of potentials is obtained and recorded after said product has returned to its original temperature.

25. A process as set forth in claim 22 in which said product is under stress during the obtaining of one set of said potentials.

26. A process as set forth in claim 21 in which said product is under stress during the obtaining of one set of said potentials.

27. A process for determining the relaxation time required for recovery of a manufactured, electrically conductive product from a stress, less than the elastic limit of the material of said product, applied thereto which comprises: obtaining a set of mechanogalvanic potentials characteristic of each of a plurality of constituent elements in said product, recording said potentials, subjecting said product to a stress less than the elastic limit of the materials thereof, discontinuing the application of said stress, and thereafter repeatedly obtaining and recording sets of mechanogalvanic potentials until said potentials approximate those obtained initially.

* * * * *

UNITED STATES PATENT AND TRADEMARK OFFICE
CERTIFICATE OF CORRECTION

PATENT NO. : 4,133,722
DATED : January 9, 1979
INVENTOR(S) : Minas Ensanian

It is certified that error appears in the above-identified patent and that said Letters Patent are hereby corrected as shown below:

In Column 1, line 54 "transistors" has been changed to --transitions--

Column 2, line 3 "produce" has been changed to --product--

Column 2, line 6 "MPG" has been changed to --MGP--

Signed and Sealed this

Twenty-ninth Day of April 1980

[SEAL]

Attest:

SIDNEY A. DIAMOND

Attesting Officer

Commissioner of Patents and Trademarks